(12) United States Patent
Camisasca (10) Patent No.: US 12,194,097 B2
(45) Date of Patent: Jan. 14, 2025

(54) WATER IRRADIATED WITH ELECTROMAGNETIC ENERGIES FOR USE AS A MEDICAMENT

(71) Applicant: LWP Life Water Prevention SRL, Milan (IT)

(72) Inventor: Luigi Camisasca, Santa Margherita Ligure (IT)

(73) Assignee: LWP Life Water Prevention SRL, Milan (IT)

( * ) Notice: Subject to any disclaimer, the term of this patent is extended or adjusted under 35 U.S.C. 154(b) by 1102 days.

(21) Appl. No.: 17/053,807

(22) PCT Filed: May 7, 2019

(86) PCT No.: PCT/EP2019/061698
§ 371 (c)(1),
(2) Date: Nov. 9, 2020

(87) PCT Pub. No.: WO2019/215165
PCT Pub. Date: Nov. 14, 2019

(65) Prior Publication Data
US 2021/0228718 A1 Jul. 29, 2021

(30) Foreign Application Priority Data
May 7, 2018 (IT) .................. 102018000005117

(51) Int. Cl.
| | | |
|---|---|---|
| C02F 1/30 | (2023.01) | |
| A61K 33/00 | (2006.01) | |
| A61K 33/14 | (2006.01) | |
| A61K 41/00 | (2020.01) | |
| A61P 25/00 | (2006.01) | |
| A61P 25/04 | (2006.01) | |

(52) U.S. Cl.
CPC .......... *A61K 41/0004* (2013.01); *A61K 33/00* (2013.01); *A61K 33/14* (2013.01); *A61P 25/00* (2018.01); *A61P 25/04* (2018.01)

(58) Field of Classification Search
None
See application file for complete search history.

(56) References Cited

FOREIGN PATENT DOCUMENTS

| CN | 101678135 | * 3/2010 |
|---|---|---|
| EP | 1653963 | 5/2006 |
| WO | WO 2005/009442 | 2/2005 |
| WO | 2007139103 | * 12/2007 |
| WO | WO 2019/215165 | 11/2019 |

OTHER PUBLICATIONS

International Preliminary Report on Patentability Dated Aug. 17, 2020 From the International Preliminary Examining Authority Re. Application No. PCT/EP2019/061698. (58 Pages).
International Search Report and the Written Opinion Dated Sep. 10, 2019 From the International Searching Authority Re. Application No. PCT/EP2019/061698. (11 Pages).
Crosta "What You Should Know About Dehydration: Symptoms Causes Risk Factors Complications Diagnosis Treatments Prevention", Medical News Today, XP055547044, p. 1-7, Last Updated Dec. 20, 2017.
Geesink "A Quantum Model About the Mechanisms Generating Biological Effects Caused by Natural and Man-Made Non-Ionizing Radiation and Possible Solutions to Restore Weel Being", Brainport Biotech Solutions, Eindhoven, The Netherlands, p. 1-9, Feb. 2013.
Giusti et al. "Effect of Repeated Application of Low-Intensity Pulsed Electromagnetic Fields (PEMF) on Gait Speed in Older Adults With A History of Falls", Journal of the American Geriatrics Society, JAGS, 62(6): 1185-1186, Jun. 2014.
Hawker et al. "Measures of Adult Pain", Arthritis Care & Research, 63(S11): S240-S252, Nov. 2011.
Issenman et al. "Oral and Intravenous Rehydration of Children", Canadian Family Physician, Medecine de Famille Canadien, XP055613408, 39: 2129-2136, Oct. 1993.
KHIS "Drink Water Instead", Kidney Health Information Service, KHIS, XP055547457, p. 1-4, Last Reviewed Nov. 2015.
Office Action Dated Dec. 20, 2022 From the Israel Patent Office Re. Application No. 278520. (4 Pages).

* cited by examiner

*Primary Examiner* — Sheng H Davis (57) ABSTRACT

The present invention relates to water for use as a medicament, characterized in that to the water, electromagnetic energies in the form of:

(i) light energy with a wavelength of between 500 and 700 nm, (ii) light energy with a wavelength of between 701 and 1050 nm, and (iii) an electrical energy with a maximum voltage of 240 V, are simultaneously applied, wherein at least one of the electromagnetic energies (i), (ii) and (iii) is applied to the water in the form of trains of pulses having at least two discrete frequencies, wherein a first frequency is between 0.1 to 10 Hz and a second frequency is between 40 and 1500 Hz.

9 Claims, 2 Drawing Sheets

WATER IRRADIATED WITH ELECTROMAGNETIC ENERGIES FOR USE AS A MEDICAMENT

RELATED APPLICATIONS

This application is a National Phase of PCT Patent Application No. PCT/EP2019/061698 having International filing date of May 7, 2019, which claims the benefit of priority of Italian Patent Application No. IT102018000005117 filed on May 7, 2018. The contents of the above applications are all incorporated by reference as if fully set forth herein in their entirety.

FIELD AND BACKGROUND OF THE INVENTION

The present invention relates to water irradiated with electromagnetic energies, a method for providing said water, which water is for use as a medicament.

For many years now, medical research has been intensely engaged in searching for tests or criteria to be able to identify the best indicator of risk prediction of falling by examining a walking subject.

To date, the best predictive factor remains the response in the patient's medical history, having previously had a fall episode, Jill Jin et al. 'Prevention of Falls in Older Adults' JAMA Apr. 24, 2018.

It has been known for a long time that if postural competence is reduced in every walking subject, the risk of falling increases. In particular, after the age of 65, postural abilities decrease with the increase of age, of the pathologies present and with the number of drugs taken (M Tinetti et al N Engl J Med 1988).

However, it is evident the limited role of improvement in postural capacity obtained by calcium and vitamin D supplementation; Bischoff-Ferrari et al 'Preventing Fractures and Falls: a limited Role for Calcium and Vitamin D Supplements" jAMA 2018 Apr. 17, 319(15)1552/1553.

More than 400 fall risk factors have been identified and the list of diseases and drugs is much wider than this list:
neurodegenerative diseases, vascular cognitive impairment, dizziness, Parkinson's, diabetes, urinary incontinence, low BMI, obesity, sarcopenia, fear of falling, hearing loss, loss of vision, walking with support, previous fractures of frailty, previous falls not associated with pathology, osteoporosis,/osteopenia, reduction of mobility on a chronic painful basis, fibromyalgia, arthrosis, polyarthritis among pathologies; antihypertensive therapy, antidepressants, benzodiazepines, hypnotics, neuroleptics and use over 4 medicines of any kind); K. Khanuja and Al Maturitas 110 (20018) 51/56 "Gait and balance in the aging population: Fall prevention using innovation and technology".

H. B. Mark et al., in The Merck Manual of Geriatrics, third Ed. 2000, pages 195-203, reports that at least 30% of people over 65 not living in hospitals experience falls at least once a year. Balance control is essential for performing everyday voluntary movements. Increasing age involves a higher risk of falling, due to bad posture.

Unstable balance related to age is negatively affected by possible pathological conditions and by unfavorably environmental and pharmacological conditions: in some cases, even stability perception is impaired. Aizen, E., in Cautious Gait and Fear of Falling in the Elderly Harefuah November 2001, 140 (11): 1091 4-1115, reports that falling often involves a reduction in mobility, due to the fear of falling again.

It is therefore apparent that improving the sense of balance and thereby limiting the possibility of falls would result in a great improvement of life conditions and possibly even in a longer life.

From the above, it is apparent that improvement in posture control would result in a reduction of falls in elderly people. Posture control concerns all the static-dynamic processes affecting the position of a body in space and the parts of said body in reciprocal motion, maintaining the specific orientation with respect to the force of gravity. The function of the central nervous system is to transform an irregular flow of impulses into a regular activation, which is governed by suitable neuromotor nuclei.

The nervous signals that originate during motion were defined as a whole as proprioceptive sensitivity by Charles Sherrington in 1906. According to this definition, suitable stimuli are applied by the body to specific receptors, which are located within movement organs. Proprioceptive sensitivity refers to different kinds of stimuli: contact, pressure, pain. All the information collected through proprioceptors is an essential element for programming and controlling stillness and movement. The most important proprioceptors are neuromuscular spindles and Golgi tendon organs, which are stretch receptors. Spindles are a highly specialized structure, widely distributed in the muscle parenchyma of skeletal muscles. Such a structure consists of a bundle of muscle fibres, enclosed in a capsule. Any muscle stretching is perceived by intrafusal fibres. Neuromuscular spindles are type 1 receptors, responding to energy changes with an electrical potential called "generating potential". Spindle sensitivity to stretching is very high and is extremely important in the perception of one's position and orientation. A suitable action on proprioceptors is very important to achieve good posture control.

In recent years, great efforts have been made to find the best action on proprioceptors. Kramer, A., in Demography and Health Status; Geriatric Medicine, Second Ed. 1996; 18-27 and Herbert, D. R. et al.; Effective Physiotherapy BMJ, vol. 323, pages 788-790, showed that through proprioceptive stimulation involving muscle exercises for the legs, improvement of motor performance can be achieved. However, Studenski, S., in Guest Edition Clinics in Geriatric Medicine, November 1996, Gait and Balance Disorders, 635-658, pointed out that there is no correlation between muscle strengthening and balance. In any case, muscle training is presently the most common treatment for improving the sense of balance.

The sense of balance may also be improved by treating a patient with different types of electromagnetic energies by means of a medical neurological instrument as disclosed in EP 2 533 857 B.

SUMMARY OF THE INVENTION

It is the object of the present invention to provide a medical use which renders possible to improve a patient's sense of balance and/or relief a patient's pain, as well as a method for preparing the means or medicament for this medical use. The improvement of the sense of balance may be assessed by testing walking parameters and/or by a push test. The relief of pain may be assessed by a visual analogue scale (VAS).

In particular, it was surprisingly found that it can be dispensed with treating a patient in need of improvement of the sense of balance and/or relief of pain directly with the medical neurological instrument disclosed in EP 2 533 857 B1. Rather, according to the present invention, if particular, selected electromagnetic energies are applied to water, then the water can be used as a medicament, in particular for treating patients having one or more diseases negatively affecting the sense of balance. Alternatively or additionally, the water for use as a medicament may be used in the treatment of pain.

Hence, owing to the present inventive concept of water for use as a medicament and a method for preparing this water, it is no longer necessary for the patient to burdensome travel for visiting a medical facility such as a hospital for obtaining a treatment by a medical neurological instrument. Rather, the patient can obtain the presently claimed water for use as a medicament, which water is provided by the present method, for example as a shipment by a postal service, or from a local pharmacy. Hence, this significantly facilitates the treatment for the patient, and it also significantly reduces costs for the healthcare system.

DESCRIPTION OF THE INVENTION

The object is achieved by the present invention by means of water for use as a medicament, characterized in that to the water, electromagnetic energies in the form of:
(i) light energy with a wavelength of between 500 and 700 nm,
(ii) light energy with a wavelength of between 701 and 1050 nm, and
(iii) an electrical energy with a maximum voltage of 240 V,
are simultaneously applied,
wherein at least one of the electromagnetic energies (i), (ii) and (iii) is applied to the water in the form of trains of pulses having at least two discrete frequencies, wherein a first frequency is between 0.1 to 10 Hz and a second frequency is between 40 and 1500 Hz,
wherein for each of light energies (i) and (ii), the amount of energy is between 1.5 to 2 J, and for the electrical energy (iii), the amount of electrical energy is up to 0.4 J.

Furthermore, according to the present invention, a method for providing water is provided which renders possible the provision of water which may be used for the aforementioned medical use. This method comprises:
(A) a step of providing water;
(B) a step of applying electromagnetic energies to the water of step (A), wherein the electromagnetic energies are in the form of:
(i) light energy with a wavelength of between 500 and 700 nm,
(ii) light energy with a wavelength of between 701 and 1050 nm, and
(iii) an electrical energy with a maximum voltage of 240 V,
and the electromagnetic energies are simultaneously applied to the water,
wherein at least one of the electromagnetic energies (i), (ii) and (iii) is applied to the water in the form of trains of pulses having at least two discrete frequencies, wherein a first frequency is between 0.1 to 10 Hz and a second frequency is between 40 and 1500 Hz,
wherein for each of light energies (i) and (ii), the amount of energy is between 1.5 to 2 J, and for the electrical energy (iii), the amount of electrical energy is up to 0.4 J.

The term "simultaneously applied" as used herein in connection with the application of electromagnetic energies (i), (ii) and (iii) means that the energies (i), (ii) and (iii) are applied during one application round where the water is applied with the aforementioned energies. However, it is self-evident that "simultaneously applied" does not mean that all electromagnetic energies (i), (ii) and (iii) must be applied simultaneously during the whole application round. Rather, from the further condition defined in claim 1 requiring that at least one of the electromagnetic energies (i), (ii) and (iii) is applied to the water in the form of pulses having at least two discrete frequencies, it is readily understood that when pulses with frequencies are applied, there may always be a point of time were the pulse is off and thus the at least one pulsed energy is not applied. In conclusion, the term "simultaneously applied" means that all three electromagnetic energies (i), (ii) and (iii) are applied during one application round, but it does not require that each electromagnetic energy (i), (ii) and (iii) is applied at the same time.

The present inventors surprisingly found that the above described electromagnetic energies (i), (ii) and (iii), which are conventionally directly applied to a patient by means of a medical neurological instrument such as that disclosed in EP 2 533 857 B1, can, without wishing to be bound to theory, be kind of "stored" in water.

It is noted that from the quantum electrodynamic theory of water put forward by Professor Emilio Del Giudice, who was a capacity in the field of water research, it is known that water can store electromagnetic energies in stable coherent domains, which may account for the so-called "memory of water". The summarized work of Professor Emilio Del Giudice in the field of water is disclosed in the review article of Mae-Wan Ho, "Illuminating Water and Life", Entropy 2014, vol. 16, pages 4874 to 4891.

However, despite of the fact that it is known in the art that water may theoretically store electromagnetic energies, it was a surprising finding for the present inventors that the electromagnetic energies are stored by the water in such a way that there is a storage for a long period of time of at least one month or more, preferably 2 months or more. Hence, owing to the method according to the invention, water can be provided which stores the electromagnetic energies applied thereto for a significant period of time.

Besides, an even more surprising finding for the present inventors was that these electromagnetic energies stored in the water are released from the water and suitably transferred to the body of the patient in such a way that the electromagnetic energies released from the water have a similar or even identical effect on the patient compared with the direct treatment of a patient by a medical neurological instrument as disclosed in EP 2 533 857 B1. This release of the electromagnetic energies could not be extrapolated from the known quantum electrodynamic theory of water put forward by Professor Emilio Del Giudice.

It is preferred that the water prepared with the method according to the present invention is applied for use as a medicament in the treatment of one or more diseases negatively affecting the sense of balance. Because, it was surprisingly found that the present water for use as a medicament is particularly effective for improving the sense of balance. More preferably, the present water for use as a medicament is used in the treatment of at least one disease selected from the group consisting of arthrosis, polyarthrosis, arterial hypertension, fibromyalgia, rheumatoid arthritis, frequent falls, vertebral fractures, diabetes mellitus, osteoporosis, recurrent falls, Alzheimer's disease, Parkinson's disease, anxiety neurosis; preferably at least one disease selected from the group consisting of arthrosis, polyarthrosis, arterial hypertension, fibromyalgia, rheumatoid arthritis, vertebral fractures, diabetes mellitus, osteoporosis, Alzheimer's disease, and Parkinson's disease; most preferably at least one disease selected from the group consisting of arthrosis, polyarthrosis, arterial hypertension, fibromyalgia, rheumatoid arthritis, vertebral fractures, diabetes mellitus, and osteoporosis.

The improvement of the sense of balance of a patient may be assessed by determining walking parameters. The testing of walking parameters is well known in the field of medicine. For example, J. M. Hausdorff, "Gait variability: methods, modeling and meaning", Journal of NeuroEngineering and Rehabilitation 2005, 2:19, discloses walking parameters, their meaning and methods for testing. Alternatively or in addition to the determination of walking parameters, a push test may be carried out for assessing whether or not there is an improvement of the sense of balance of a patient. The push test may be carried out by applying a push with a defined push force to a certain region of the patient's body, such as belly or between the shoulders, and then studying whether or not the patient can keep balance.

Alternatively or additionally to the treatment of the above listed one or more diseases negatively affecting the sense of balance, according to the present invention, the water for use as a medicament may be used in the treatment of pain. Namely, it was surprisingly found that the present water for use as a medicament is, besides of the treatment of the aforementioned diseases, also particularly effective for relieving pain. Preferably, the present water for use as a medicament is used in the treatment of at least one pain selected from myofascial pain, central sensitization pain, chronic pain, algo-dysfunctional pain, acute pain, neuropathic pain, nociceptive pain including post-surgical pain inflammatory pain, osteoarthritis and visceral pain, more preferably at least one pain selected from myofascial pain, algo-dysfunctional pain and chronic pain, even more preferably myofascial pain and benign chronic pain (secondary algo-dysfunctional syndrome), most preferably myofascial pain.

The relief of pain may for example be assessed by means of visual analogue scale (VAS). In the field of medicine, VAS is a well known measure for pain assessment, and a description of the VAS method can for example be found in the following review article: M. Haefeli, A. Elfering, "Pain assessment", Eur. Spine J. 2006, vol. 15, pages 17 to 24.

The term "water" as used herein means, from the chemical point of view, $H_2O$. The water may comprise further intended or occasional components. Typically, the water will comprise at least traces of inorganic salts composed of cations of e.g. Sodium, Potassium, Magnesium, Calcium, Aluminium, Iron, Copper, Zinc and Lead, and anions such as chloride, fluoride, (hydrogen)carbonate, sulphate, nitrate and phosphate.

All features relating to the water disclosed in the following refer both to the present medical use as well as to the method for preparing water.

In the present invention, the water may be in the form tab water, distilled water, osmosis water, reverse osmosis water, or a mixture thereof. Preferably, the water is in the form of tap water, since tap water is readily available and economic, and the typical components of tap water do not impair the effects of the present invention. However, for specific purposes such as scientific studies requiring a reliable reproducibility, it is preferred to use processed water selected from distilled water, osmosis water and reverse osmosis water, wherein the processed water should always be obtained from the same supplier, and at best be from the same production batch.

Depending on how the water is applied to a patient in need of a therapy, a physiological acceptable organic or inorganic salt may be intentionally added to the water. For example, in case the water shall be applied by injection with a syringe, e.g. intravenous injection, it is preferred that sodium chloride is added to the water in order to be compatible with the blood of the patient. On the other hand, in case the water is applied onto the human skin, it may be advantageous to add an organic salt providing for a pleasant odor and/or pleasant color, since odor and color of the water may provide for a good, relaxed feeling of the patient.

In case a physiological acceptable organic or inorganic salt is added to the water, it is preferred that the water contains the physiological acceptable organic or inorganic salt in an amount of at most 330 g/l, preferably 1 to 35 g/l, more preferably 4 to 30 g/l, most preferably 8 to 10 g/l. The broader value ranges for the amount of the physiological acceptable organic or inorganic salt are selected in view of providing a pleasant odor, pleasant color, or pleasant "Dead Sea"-feeling. The lowermost value range of 8 to 10 g/l is selected in view of a good compatibility with body fluids such as blood, in case the water is applied by injection with a syringe, e.g. intravenous injection.

According to the present invention, the water may be in the form of water alone or comprised in a material selected from a fabric, a non-woven, medical patches, a cream formulation, a gel formulation, an ointment formulation, an aqueous solution, a product for dental hygiene, a food and a drink.

The term "water alone" as used herein means "water" as defined above, that is, further components such as e.g. organic or inorganic salts may be comprised in the water. Hence, the term "water alone" encompasses any aqueous solution.

The kind of application of the water to a patient in need of treatment therewith, namely water alone or water comprised in a material, depends on how the water shall be used as a medicament. In case it is intended to treat locations in the inner side of the patient's body, it is preferred to apply the water by injection with a syringe, e.g. intravenous injection, or as a drink or food. In the aforementioned cases, the water is preferably used alone without comprising it into one of the above listed selected materials.

On the other hand, in case it is intended to treat an external part of the patient's body, for example by applying the water onto the patient's skin, it is helpful to comprise the water into one of the above listed materials to provide for a simple and convenient application, e.g. on the skin. For application onto the skin of the body portion to be treated, it is preferred to comprise the water in a fabric, more preferred in gauze or a terry fabric, most preferred in a gauze. Alternatively or additionally, for application onto the skin, a cream formulation, a gel formulation or an ointment formulation comprising the water according to the present invention may be used.

In case the water is comprised in one of the above listed selected materials, the water if preferably already comprised in the material when the water is applied with the electromagnetic energies. Alternatively, after applying the electromagnetic energies to the water, the water may be incorporated into the above listed selected materials.

It was surprisingly found that even if the water is comprised in a pharmaceutical composition, the active ingredients, irrespective whether there are one or a mixture of two or more active pharmaceutical ingredients, do not negatively affect the surprising effects of improving the sense of balance and relieving/decreasing pain. Rather, even if active pharmaceutical ingredients are contained in the water, the patient benefits from aforementioned effects for at least 7 to 10 days.

Preferably, the pharmaceutical composition is selected from the group consisting of Gentamicin®/Bematamethasone® cream, Connectivina® cream, Oxivan® cream, Zovirax® cream, Aciclin® cream, Edeven® gel; Flector Artro® gel, Orudis® gel, Tetramyl® eye drops drops, Otalgan® drops, Bioderm® paste breathable barrier, Nivea® cream, Prep® cream, Preparation H® ointment, Rinazina® spray, Salonpas® spray and Esteè Lauder advance night Repair®.

Furthermore, it was surprisingly found that the application of the electromagnetic energies (i) to (iii) to water comprised in a pharmaceutical composition, for example the above indicated and presently tested compositions, does not negatively affect the pharmaceutical effectiveness of the pharmaceutical composition. That is, the active pharmaceutical ingredient contained in the pharmaceutical composition is not deteriorated due to the treatment with electromagnetic energies (i) to (iii).

All features relating to the electromagnetic energies (i), (ii) and (iii) applied to the water and disclosed in the following refer both to the present medical use as well as to the present method for preparing water.

Preferably, the electromagnetic energies (i), (ii) and (iii) are simultaneously applied for at least 5 min, preferably 7 min to 2 h, more preferably 8 min to 1 h, even more preferably 9 min to 35 min, yet even more preferably 9 min to 30 min, most preferably 10 to 20 min. It was surprisingly found that already a relative short application time of only about 5 min provides for a sufficient amount of energy stored for the present medical use.

It is preferred that the time for applying the electromagnetic energies (i), (ii) and (iii) to the water is selected such that a sufficient amount of energy is applied to the water for storage in the water and further use of the resulting water as a medicament. The amount of light energies (i) and (ii) may be calculated from the following well known formula:

$$E_{light} = (h \cdot c/v) \cdot t,$$

wherein h is the Planck constant, c is the speed of light in vacuum, v is the wavelength of the light, and t is the time period used for applying the light energies (i) and (ii). The amounts of light energies (i) and (ii) have the unit Joule (J). Furthermore, the amount of electrical energy (iii), which may also be termed electrical work, may be calculated from the following well known formula:

$$E_{electric} = U \cdot I \cdot t,$$

wherein U is the voltage, I is the current, and t is the period of time for which the electrical energy (iii) is applied. The amount of electrical energy (iii) has the unit Watt seconds (W·s) or Joule (J).

For the amount of at least one electromagnetic energy (i), (ii) and (iii) applied to the water in the form of trains of pulses having at least two discrete frequencies, it is clear that the amount of energy applied is not the full period of time for which any one of these energies is applied, but the frequencies have to be taken into consideration, and optionally additionally pause times.

As derivable from the aforementioned formulae, independent from the kind of energy, the amount of each energy (i) to (iii) applied to the water depends on the period of time for which the light according to (i) and (ii) and the electrical energy according to (iii) is applied, which period of time depends on the kind and severity of disease to be treated.

For each of light energies (i) and (ii), the amount of energy of 1.7 to 1.9 J is preferred. For the electrical energy (iii), it is preferred that the amount of electrical energy is 0.05 to 0.3 J, more preferably 0.1 to 0.25 J.

The present water for use as a medicament may be applied to a person in need of the treatment for a predetermined time, which depends on the severity of the disease of the person and the person as such in terms of size, weight and age, which aforementioned conditions may be assessed by a doctor's prescription. Preferably, the present water for use as a medicament is applied to a person in need of a treatment for at least 10 min, preferably 15 min to 2 h, more preferably 15 min to 1 h, most preferably 15 min to 30 min. Surprisingly, already a relatively short application time of 10 min is sufficient for providing a significant therapeutical effect.

The pulse of at least one of energies (i), (ii) and (iii), the duration of the pulse and the voltage of (iii) the electrical energy is selected in view of the severity of the disease(s) of the person in need of a treatment.

Preferably, the pulses have at least two discrete frequencies, the first frequency is between 0.3 to 7 Hz and the second frequency is between 55 and 800 Hz. More preferably, the first frequency is between 0.5 to 5 Hz and the second frequency is between 70 and 200 Hz. Even more preferably, the first frequency is between 0.8 to 3.2 Hz and the second frequency is between 80 and 190 Hz. Yet even more preferably, the first frequency is 1 Hz, 2 Hz or 3 Hz, and the second frequency is 85 Hz, 100 Hz or 180 Hz. Most preferably, the first frequency is 1 Hz and the second frequency is 180 Hz, the first frequency is 2 Hz and the second frequency is 100 Hz, or the first frequency is 3 Hz and the second frequency is 85 Hz.

Particularly preferred are pulses having more than two discrete frequencies, which numerical value ranges are selected from the numerical value ranges indicated in the claims and the description text above for the first and second frequency. For example, such pulse having more than two discrete frequencies may have 4 discrete frequencies #1 to #4, namely frequencies #1 and #2 being within the numerical value range of 0.1 to 10 Hz of the above indicated first frequency, and frequencies #3 and #4 being within the numerical value range of 60 and 220 Hz of the above indicated second frequency. That is, as an explanatory example, frequencies #1 to #4 may be as follows: A frequency #2 of 0.5 to 1.5 Hz, a frequency #2 of 2.0 to 4.0 Hz, a frequency #3 of 80 to 120 Hz, and a frequency #4 of 16 to 200 Hz. Optionally, said pulses having more than two discrete frequencies may additionally have a further frequency with a value range being outside the numerical value ranges for the above defined value ranges for the first and the second frequency.

It was surprisingly found that pulses having at least two discrete frequencies are particularly effective for improving the patient's sense of balance in terms of walking parameters and postural parameters. Furthermore, it was surprisingly found that pulses having at least two discrete frequencies are particularly effective for improving for relieving/decreasing mysofascial and/or algo-dysfunctional pain.

Preferably, each pulse has a duration of between 50 and 1000 µs, more preferably of between 80 and 500 µs, most preferably of between 90 and 350 µs.

It is preferred that between the pulses, there is a pause time of between 0.5 and 20 s during which there is no pulsed discrete frequency.

For the light energies (i) and (ii), it is preferred that light energy (i) has a wavelength of between 450 and 700 nm, and light energy (ii) has a wavelength of between 750 and 1000 nm. More preferably, light energy (i) has a wavelength of between 550 and 660 nm, and light energy (ii) has a wavelength of between 850 and 980 nm. Most preferably, light energy (i) has a wavelength of between 580 and 645, and light energy (ii) has a wavelength of between 870 and 920 nm. The light energy (i) and/or (ii) may be in monochromatic, coherent or incoherent form.

Preferably, the electrical energy (iii) has a maximum voltage of 200 V, more preferably a maximum voltage of 150 V, even more preferably a maximum voltage of 110 V, yet even more preferably a maximum voltage of 90 V, and most preferably a maximum voltage of between 50 and 85 V. Furthermore, for the electrical energy (iii), preferably the current is up to 0.6 mA, more preferably 0.1 to 0.5 mA, most preferably 0.25 to 0.4 mA.

It is preferred that when the water for use as a medicament according to the present invention is used for improving the sense of balance, to apply any one of the electromagnetic energies (i), (ii) and (ii) in pulses for a time of between 30 s and 30 min, more preferably between 45 s and 10 min, most preferably between 1 min and 5 min.

For use in the treatment of pain, it is preferred that the water for use as a medicament according to the present invention is applied to a patient for a time period of between 2 min and 2 hours, more preferably between 4 min and 30 min, and most preferably between 5 min and 15 min. This time period is particularly useful for alleviating pain in the cervical region, in the lumbar region and for treating osteoarthritis.

For the present method for providing water, it is preferred that the water resulting from this process is used as a medicament. For example for the aforementioned purpose, the present method preferably further comprises:

(C) an optional step of storing the water obtained in step (B) until it is used for any optional purpose, for example as a medicament; and (D) an optional step of using the water of step (B) or (C) as a medicament.

BRIEF DESCRIPTION OF THE SEVERAL VIEWS OF THE DRAWINGS

For a better understanding of the present invention, in the following, a particularly suitable device for applying electromagnetic energies (i), (ii) and (iii) to the water is described.

Figure 1:
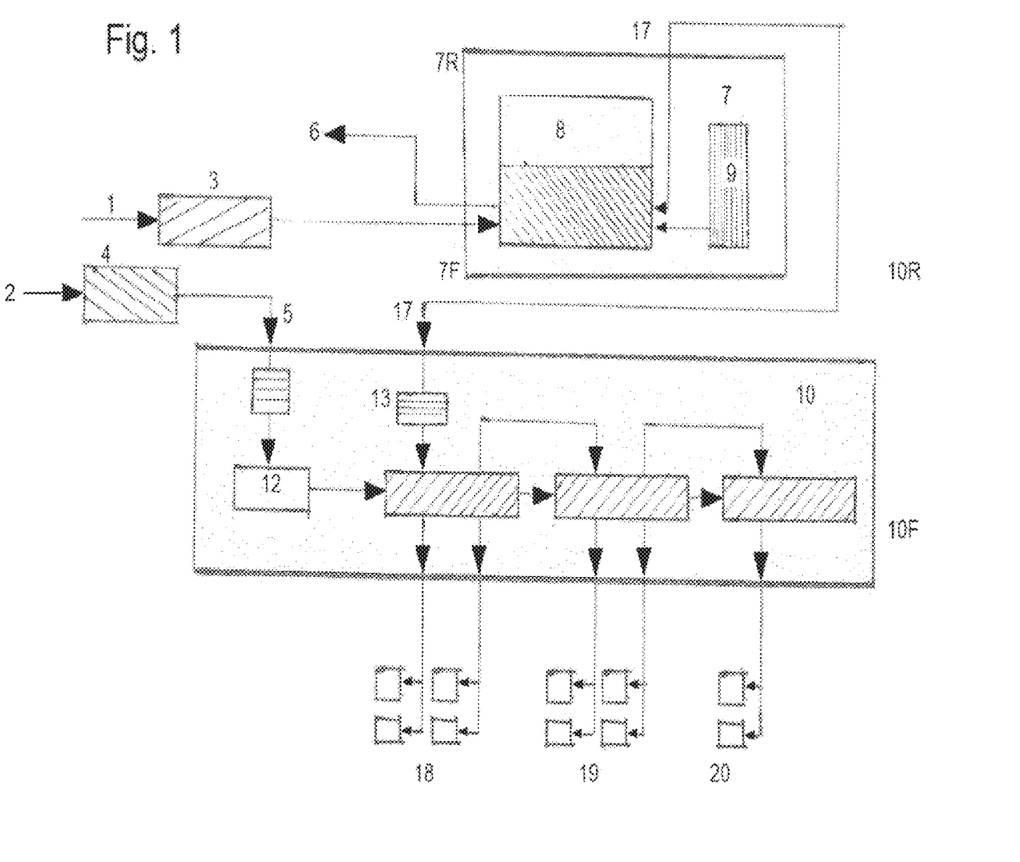
FIG. 1 shows the schematical structure of a medical neurological instrument which may be used as device for applying electromagnetic energies (i), (ii) and (iii) to the water.

LEGEND OF FEATURES OF THE MEDICAL NEUROLOGICAL INSTRUMENT ILLUSTRATED IN FIG. 1

1 Power cable connected to power supply 3, which supplies direct current voltage to charge the batteries of notebook 8;

2 Power cable connected to power supply 4 to charge the batteries 12 of medical device (MD) 10;

3 Notebook power supply suitable to convert the 220 V mains voltage into 18 V direct current to charge the battery of notebook 8;

4 Power supply and battery charger 4 to convert the 220 Vac mains voltage into 14 volt direct current voltage to charge the battery of MD 10;

5 Metal panel socket mounted on MD 10R to carry voltage into the container of the MD 10 connected to the safety device 11, which performs the function of shutting off the power of MD 10 in the event of insertion of the plug of power supply of MD 10;

6 Output connector for LAN/internet connection;

7 Metal container suitable to support or transport of notebook and badge reader with openable compartments designed to house cables;

7R Rear panel of the notebook container with feet and reinforcements for safe transport;

7F Front panel of the notebook container with locks and reinforcing handles for safe transport;

8 Notebook;

9 Badge reader used for immediate recognition or storage of patient's data which will be stored in a database in notebook 8;

10 MD in the form of a metal container suitable to contain all circuit boards 14, 15, 16 of safety device 11 and battery 12, as well as RS232/USB communication interface 13;

10R MD 10 rear panel suitable to house power socket 5 and USB socket 17;

10F MD front panel suitable to house all light signals and connectors, mechanically interlocked, to convey, by means of connection cables, signals supplied to transducers 18, 19, 20;

11 Safety device that immediately shuts off operation of MD 10, if power plug from power supply 4 is inserted during charging of internal battery 12;

12 12 volt battery, which is the sole power source for operation of MD 10;

13 RS232/USB interface, which transforms USB commands from notebook 8 into communication signal for all boards 14,15,16;

14 first energy pulse generator board;

15 second energy pulse generator board;

16 third energy pulse generator board;

17 USB socket which, through USB cable connected to socket 17 positioned on MD rear panel 10R, conveys the commands for boards 14, 15, 16 through interface 13 positioned inside container 10;

18 First energy transducers connected with cable and metal connector positioned on panel 10F of container 10;

19 Second energy transducers connected with cable and metal connector positioned on panel 10F of container 10; and 20 Third energy transducers connected with cable and metal connector positioned on panel 10F of container 10.

DESCRIPTION OF THE SPECIFIC EMBODIMENTS OF THE INVENTION

Preferably, the medical neurological instrument comprises:

(A) a control system for managing energy sources of different nature, and (B) an emitter of said energy sources, wherein the emitter is configured to simultaneously apply electromagnetic energies in the form of:
  (i) light energy (18) with a wavelength of between 500 and 700 nm,
  (ii) light energy (19) with a wavelength of between 701 and 1050 nm, and
  (iii) an electrical energy (20) with a maximum voltage of 240 V,
wherein at least one of the electromagnetic energies (i), (ii) and (iii) is applied in the form of trains of pulses having at least two discrete frequencies, wherein a first frequency is between 0.1 to 10 Hz and a second frequency is between 40 and 1500 Hz, and wherein the control system (A), which is a computer having dedicated software, manages the strength, frequency and duration of these energies.

Preferably, the transducers 18, 19, 20 comprise semiconductive light emitters with fixed emission of 2000 mcd, where these emitters are divided into three groups of at least two units each, so as to repeatedly emit pulses every 2, 4 and 8 sec respectively. The duration of the single pulse is preferably 50-1000 ms, more preferably 80-500 ms, even more preferably 90-350 ms.

According to the present invention, the electromagnetic energies comprise (iii) the electrical energy. The electrical energy (iii) may be provided e.g. by means of a pair of electrodes.

The strength, frequency and duration of the pulses are controlled from the notebook 8, which, with a specifically developed software program, manages operation thereof. In order to use the device in the form of the above described medical neurological instrument correctly, it is essential for the three energy sources to be used simultaneously in order to obtain a beneficial effect for the patient, wherein the three energies are variable and are preferably suitably selected by a doctor in view of the pathological conditions. The device thus allows the operator to dose the strength, frequency and duration of the pulses for each of the energy sources, obtaining a synergic combination of these sources, which can be optimized for the specific pathological conditions encountered and which can also be customized for each patient. The interface with internet 6 also allows interaction and exchange of therapeutic programs, in real time, with the various experiences of the physicians using it, thus allowing the creation of a sort of interactive database in which information on each treatment can be saved, to the benefit of the next operator who wishes to receive information and advice on parameters to use. The aforesaid optimization is therefore shared and can benefit from a plurality of experimental contributions.

Preferably, the medical neurological instrument comprises six emitters, of which two emitters repeatedly emit pulses every 2 sec., two emitters repeatedly emit pulses every 4 sec. and two emitters repeatedly emit pulses every 8 sec. In other words, the difference in the behavior of the emitters is found only in the duration of the interval between one pulse and the next. The emitters therefore emit a radiation in the region of the red and infrared wavelength.

The transducers may for example be in the form of electrodes having a negative pole on one side and a positive pole on the other side, to apply the electrical energy to the water.

Figure 2:
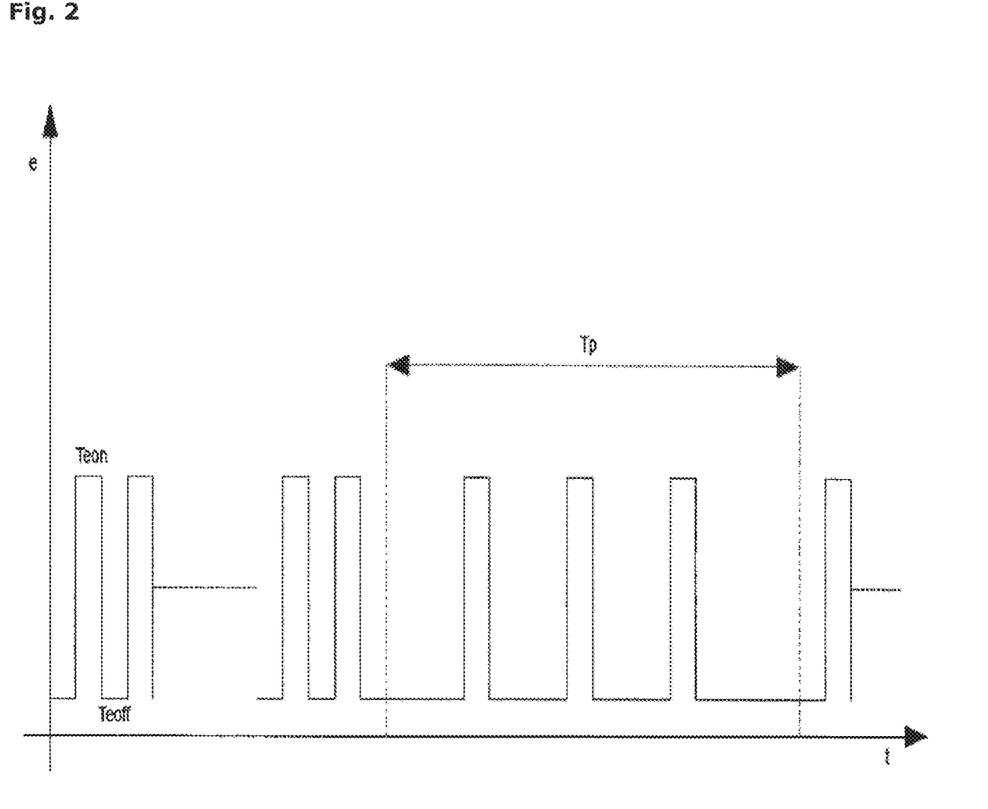
FIG. 2 shows a diagram of electromagnetic energy (e) applied by the medical neurological instrument versus time (t) (in seconds) to illustrate an exemplary pulse applied by the medical neurological instrument.

With reference to FIG. 2, it is possible to evaluate the type of waveform applied to the transducers. The time T is represented on the abscissa, while the energy supplied e is represented on the ordinate. By varying the time $Te_{on}$ (on time), the time $Te_{off}$ (off time) and the pause time $T_p$, trains of pulses are sent with a variable period and a variable duty cycle for the three energies, determined by the therapy to be performed. It is also possible to send single energy pulses during the pause time $T_p$.

The invention will now be illustrated in detail with reference to specific experimental examples, in which a series of patients divided into groups of specific physical and pathological conditions were treated with the water for use as a medicament according to the present invention.

EXPERIMENTAL EXAMPLES

In the following examples, sense of balance was assessed by means of testing of walking parameters as well as by a push test for determining resistance to lateral thrust. In addition, a pain assessment by visual analogue scale (VAS) was carried out.

In all the present experimental examples, for the light energies (i) and (ii), the amount of energy applied was between 1.5 to 1.7 J, and for electrical energy (iii), the amount of energy applied was between 0.1 to 0.4 J, wherein for light energies (i) and (ii), the wavelengths applied were between 500 and 700 nm for energy (i) and 701 to 1050 nm for energy (ii), while for the electrical energy (iii), the voltage was between 50 V and 240 V. The times for applying the present water for use as a medicament were between 10 to 20 min, depending on the severity of the disease and/or pain to be treated. In practice, it is preferable that the doctor prescribes the conditions for the electromagnetic energies (i), (ii) and (iii) as well as the duration of the application of the present water, in order to adapt these conditions to the severity of the disease and/or pain to be treated as well as to the patient.

The electromagnetic energies applied to the water for use as a medicament according to the present invention are similar to a great extent to the electromagnetic energies conventionally applied by a medical neurological instrument as e.g. disclosed in EP 2 533 857 B. Therefore, in addition to the above indications for the specific energy ranges of electromagnetic energies (i), (ii) and (iii) applied in Joule and the treatment time for which the present water is applied to a patient for use in the treatment of a disease, a skilled person may estimate the electromagnetic energies (i), (ii) and (iii) required for a treatment with the present water based on his knowledge of suitable conditions for the conventional treatment.

In the following experimental examples, the water for use as a medicament according to the invention, was applied in different forms, namely the water was used alone, as an aqueous solution in the form of a physiologic saline solution, or comprised in a pharmaceutical or non-pharmaceutical formulation selected from the group consisting of Gentamicin®/Bematamethasone® cream, Connectivina® cream, Oxivan® cream, Zovirax® cream, Aciclin® cream, Edeven® gel; Flector Artro® gel, Orudis® gel, Tetramyl® eye drops drops, Otalgan® drops, Bioderm® paste breathable barrier, Nivea® cream, Prep® cream, Preparation H° ointment, Rinazina® spray, Salonpas® spray and Esteè Lauder advance night Repair®.

Optionally additionally, were applicable and suitable for the site of the body of the patient to be treated, the water in the form indicated above was comprised in a gauze fabric.

Testing of Walking Parameters

The walking parameters tested in the following experiments are defined as follows:

Walking speed: Self-evidently means the speed of walking of the patient;

Step length: Is the distance between the heel contact point of one foot to the other foot;

Double support: Is the amount of time that a participant spends with both feet on the ground during one gait cycle;

Base of support: Is the area beneath the patient that includes every point of contact by the feet that the object or person makes with a supporting surface; and Cadence: Is the rate at which the patient walks, expressed in steps per minute.

For the present experiments, including testing of walking speed, push test and pain assessment, 80 patients have been tested being aged 70 years or older. 40 patients treated with water according to the present invention were tested, and the other 40 patients of the placebo group were treated with normal water, i.e. water to which no electromagnetic energies were applied.

For the testing of the walking parameters, the patients were divided into five different groups, wherein the division was done in view of the patient's diseases and/or symptoms. Thereby, five groups of respectively eight persons treated with water according to the invention were tested, as well as five placebo groups of respectively eight persons.

To the patients of groups 1 to 5, the water for use as a medicament was applied in the following forms:

Patient group 1 was treated with a gel containing the active pharmaceutical ingredient (API) piroxicam, which is a type of medicine called non-steroidal anti-inflammatory drug (NSAID). NSAIDs are used to relieve pain and inflammation. In the present examples, Felden® Gel was used, but alternatively, any other, i.e. generic, comparable commercially available piroxicam gel may be used.

Patient group 2 was treated with a gel patch containing the API diclofenac epolamine, which also a NSAID. In the present examples, Voltaren® patch was used, but alternatively any other, i.e. generic, comparable commercially available diclofenac epoamine containing gel patch may be used.

Patient group 3 was treated with a moisturizer containing hyaluronic acid and glycerin. In the present examples, Neutrogena® hydro boost was used, but alternatively, any other, i.e. generic, comparable commercially available moisturizer containing hyaluronic acid and glycerin may be used.

Patient group 4 was treated with physiological aqueous saline solution having a sodium chloride concentration of 0.9%, which was administered intravenous (IV) in an amount of 100 ml respectively.

Patient group 5 was treated with a patch soaked with water only.

Regarding the walking parameters, for the increase of speed, the step length and the cadence, an increase of said parameters is a desirable improvement, while for the double support and the base of support, a decrease of said parameters is a desirable improvement.

The percentile difference of the walking parameters before and after treatment was assessed as follows: A difference of less than ±4% was assessed as (insignificant) increase/decrease, a difference of ±4% or more as significant increase/decrease, a difference of ±15% or more as very significant increase/decrease.

A desirable decrease or increase of the tested walking parameters was denoted with the positive signs "+", "++" and "+++", while an undesirable decrease or increase of the tested walking parameters was denoted with the negative signs "+", "++" and "+++"

The results of the testing of the walking parameters with the above described groups were as follows:

Patient Group 1: Polyarthric, Frequent Falls

Patients treated with water according to the present invention:

| | Speed [cm/sec] | Step length [cm] | Double support [sec] | Base of support [cm] | Cadence [steps/min] |
|---|---|---|---|---|---|
| before treatment | 45.3 | 32.745 | 0.493 | 11.37 | 82.1 |
| after treatment | 51.1 | 34.197 | 0.430 | 10.82 | 90.9 |
| difference [%] | +12.80% | +4.43% | -12.77% | -4.84% | +10.7% |
| rating of effect | ++ | + | ++ | + | ++ |

Placebo group treated with water not according to the present invention:

| | Speed [cm/sec] | Step length [cm] | Double support [sec] | Base of support [cm] | Cadence [steps/min] |
|---|---|---|---|---|---|
| before treatment | 45.7 | 32.187 | 0.468 | 16.93 | 53 |
| after treatment | 47.2 | 31.267 | 0.473 | 16.90 | 51 |
| difference [%] | -3.28% | -2.86% | -1.07% | -0.177% | -3.77% |
| rating of effect | − | − | + | + | − |

Patient Group 2: Myofascial Pain Syndrome, Recurrent Falls

Patients treated with water according to the present invention:

| | Speed [cm/sec] | Step length [cm] | Double support [sec] | Base of support [cm] | Cadence [steps/min] |
|---|---|---|---|---|---|
| before treatment | 83.3 | 52.25 | 0.287 | 11.20 | 94.2 |
| after treatment | 90.4 | 54.71 | 0.246 | 9.70 | 97.5 |
| difference [%] | +8.5% | +4.70% | -14.2% | -13.3% | +3.5% |
| rating of effect | ++ | + | ++ | + | ++ |

Placebo group treated with water not according to the present invention:

| | Speed [cm/sec] | Step length [cm] | Double support [sec] | Base of support [cm] | Cadence [steps/min] |
|---|---|---|---|---|---|
| before treatment | 73.4 | 50.27 | 0.335 | 9.27 | 68 |
| after treatment | 69.3 | 49.78 | 0.340 | 9.55 | 71 |
| difference [%] | -5.59% | -0.97% | -1.49% | +3.02% | +4.41% |
| rating of effect | −− | − | + | − | + |

Patient Group 3: Osteoporosis, Diabetes Mellitus, Vertebral Fractures

Patients treated with water according to the present invention:

|  | Speed [cm/sec] | Step length [cm] | Double support [sec] | Base of support [cm] | Cadence [steps/min] |
|---|---|---|---|---|---|
| before treatment | 58.4 | 39.440 | 0.410 | 10.78 | 91.7 |
| after treatment | 96.7 | 54.31 | 0.256 | 8.65 | 99.8 |
| difference [%] | +65.5% | +37.7% | −37.5% | −19.7% | +8.8% |
| rating of effect | +++ | +++ | +++ | ++ | ++ |

Placebo group treated with water not according to the present invention:

|  | Speed [cm/sec] | Step length [cm] | Double support [sec] | Base of support [cm] | Cadence [steps/min] |
|---|---|---|---|---|---|
| before treatment | 55.4 | 39.440 | 0.410 | 10.78 | 91 |
| after treatment | 59.8 | 38.798 | 0.387 | 11.21 | 89 |
| difference [%] | +7.94% | −1.63% | −5.61% | +3.99% | −2.20% |
| rating of effect | + | − | + | − | − |

Patient Group 4: Fibromyalgia, Rheumatoid Arthritis, Arterial Hypertension, Sarcopenia Patients treated with water according to the present invention:

|  | Speed [cm/sec] | Step length [cm] | Double support [sec] | Base of support [cm] | Cadence [steps/min] |
|---|---|---|---|---|---|
| before treatment | 75.4 | 50.03 | 0.335 | 9.27 | 56 |
| after treatment | 88.3 | 51.86 | 0.278 | 7.96 | 71 |
| difference [%] | +17.10% | +3.6% | −17.0% | −14.1% | +26.8% |
| rating of effect | +++ | + | +++ | + | +++ |

Placebo group treated with water not according to the present invention:

|  | Speed [cm/sec] | Step length [cm] | Double support [sec] | Base of support [cm] | Cadence [steps/min] |
|---|---|---|---|---|---|
| before treatment | 81.3 | 52.30 | 0.281 | 11.11 | 93.8 |
| after treatment | 80.7 | 51.77 | 0.278 | 10.98 | 92.7 |
| difference [%] | −0.74% | −1.01% | −1.07% | −1.17% | −1.17% |
| rating of effect | − | − | + | + | − |

Patient Group 5: Alzheimer's Disease, Polyarthrous, Frequent Falls

Patients treated with water according to the present invention:

|  | Speed [cm/sec] | Step length [cm] | Double support [sec] | Base of support [cm] | Cadence [steps/min] |
|---|---|---|---|---|---|
| before treatment | 44.7 | 33.197 | 0.498 | 16.93 | 53 |
| after treatment | 59.6 | 44.267 | 0.377 | 15.90 | 73 |
| difference [%] | +33.3% | +33.3% | −24.2% | −6.1% | +37.8% |
| rating of effect | +++ | +++ | +++ | + | +++ |

Placebo group treated with water not according to the present invention:

|  | Speed [cm/sec] | Step length [cm] | Double support [sec] | Base of support [cm] | Cadence [steps/min] |
|---|---|---|---|---|---|
| before treatment | 44.3 | 32.556 | 0.481 | 10.27 | 78.1 |
| after treatment | 45.1 | 32.759 | 0.477 | 10.82 | 79.0 |
| difference [%] | +1.81% | +0.62% | −0.40% | +5.36% | +1.15% |
| rating of effect | + | + | + | −− | + |

From the above experimental results, it becomes immediately apparent that in the groups treated with water according to the present invention, there is always an increase/improvement in the walking parameters, and most of the time the increase is significant or even very significant. By contrast, in the placebo group, besides of outliers, undesired decreases or only insignificant increases of the walking parameters were found.

In particular, the above experimental results show that the water for use as a medicament according to the present invention provides for:

A significant or even very significant increase of walking speed and step length, a significant or even very significant decrease of double support time and base of support, and a significant or even very significant increase of cadence.

By contrast, the placebo group treated with water being not according to the present invention shows no or at least no significant improvement of the walking parameters. Hence, it is proven that surprising therapeutically effects are attained owing to the present medical use, whereby an alleged placebo effect can be ruled out with the present experimental examples.

Further Testing of Walking Parameters

An additional testing of walking parameters was carried out, in which testing, other or modified walking parameters compared to the ones tested above were determined. This additional testing was carried out with patients other than those tested in the above described testing of walking parameters.

The walking parameters tested in the following additional experiments are defined as follows:

Walking speed over 10 meters, in seconds and as fast as the patient can: Self-evidently means the time in seconds the patient required for walking the distance of 10 meters;

TUG (Timed Up and Go) [seconds]: In the TUG test, the time to get up and go/walk is determined. This is a simple mobility test to assess the mobility or the body balance and the resulting risk of a fall, especially of elderly persons;

Semi-Tandem test [seconds]: In this test, the patient should stand for 10 seconds with one foot behind the other, so that the big toe of one foot is touching the side of the heel of the other;

Tandem test [seconds]: In this test, the patient, whose semi-tandem stand was successful, was asked to stand for 10 seconds with one foot behind the other, so that the big toe of one foot is touching the heel of the other foot;

Backward walking on 3 meters, in seconds and as fast as the patient can, Carter V. et al '*The 3 m Backwards Walk and Retrospective Falls: Diagnostic Accuracy of a Novel Clinical Measure*' *J Geriatr PhysTher* 2017.

Self-evidently, this parameter means the time in seconds the patient required for backwardly walking the distance of 3 meters; and Chair test (how many times the patient gets up and sits in 30 s):

This is the amount/sum of getting up and sitting down processes the patient was able to perform within 30 seconds.

For the additional testing of walking speed, patients have been tested being aged between 65 and 85 years or older. The 5 patients of the placebo group were treated with a placebo, i.e. water to which no electromagnetic energies (i) to (iii) were applied, without telling this to the patient. 5 other patients were treated with the water according to the present invention.

The patients number 1 to 5 of the placebo group had the following diseases and optionally additionally the following number of prescribed medicines/drugs:

Patient 1: Fibromyalgia, rheumatoid arthritis+4 medicines a day;

Patient 2: Vertebral pluri-sagging, osteoporosis, osteoarthritis, visually impaired;

Patient 3: Diabetes+4 medicines per day, fibromyalgia;

Patient 4: Rheumatoid arthritis+4 medicines per day, sarcopenia, previous cerebral ischemia; and Patient 5: Anti-depressant drugs+4 drugs a day, hypertension, osteoporosis.

| | PLACEBO group: Testing results | | | | | | | | |
|---|---|---|---|---|---|---|---|---|---|
| | PATIENT No. | | | | | | | | |
| | 1 | | 2 | | 3 | | 4 | | 5 | |
| TEST TYPE | before | after | before | after | before | after | before | after | before | after |
| Walking speed over 10 meters [seconds] | 9.27 | 9.58 | 7.43 | 7.27 | 12.39 | 11.98 | 8.55 | 9.37 | 12.81 | 13.09 |
| difference [%] | | +3.34 | | −2.15 | | −3.31 | | +9.59 | | +2.19 |
| Walking speed over 10 meters (as fast as he can) [seconds] | 10.25 | 9.99 | 8.16 | 9.22 | 13.40 | 13.17 | 10.78 | 10.55 | 14.77 | 13.98 |
| difference [%] | | −2.54 | | +12.99 | | −1.72 | | −2.13 | | −5.35 |
| TUG (Timed Up and Go) [seconds] | 12.50 | 12.65 | 11.20 | 11.25 | 12.40 | 11.55 | 16.30 | 16.80 | 13.70 | 13.18 |
| difference [%] | | +1.20 | | +0.45 | | +1.21 | | +3.07 | | −3.80 |
| TANDEM test [seconds] | >10 | >10 | >10 | >10 | >10 | >10 | >10 | >10 | >10 | >10 |
| SEMI TANDEM test [seconds] | >10 | >10 | >10 | >10 | >10 | >10 | >10 | >10 | >10 | >10 |
| Backwards walking on 3 meters [seconds] | 8.25 | 8.09 | 6.37 | 6.22 | 9.88 | 9.13 | 6.35 | 6.79 | 9.31 | 9.27 |
| difference [%] | | −1.94 | | −2.35 | | −7.59 | | +6.93 | | −0.43 |
| Backwards walking on 3 meters (as fast as he can) [seconds] | 7.31 | 7.70 | 6.90 | 7.00 | 10.67 | 9.33 | 7.55 | 7.30 | 10.29 | 9.78 |
| difference [%] | | +5.34 | | +1.45 | | −12.56 | | −3.31 | | −4.96 |
| Chair Test (times he gets up and sits in 30 seconds) | 15.00 | 14.00 | 11.00 | 10.00 | 16.00 | 17.00 | 11.00 | 12.00 | 16.00 | 15.00 |
| difference [%] | | −6.67 | | −9.09 | | +6.25 | | +9.09 | | −6.25 |

| TEST TYPE | 1 before | 1 after | 2 before | 2 after | 3 before | 3 after | 4 before | 4 after | 5 before | 5 after |
|---|---|---|---|---|---|---|---|---|---|---|
| Group treated with water according to invention: Testing results | | | | | | | | | | |
| Walking speed over 10 meters [seconds] | 11.63 | 9.45 | 11.40 | 11.36 | 15.02 | 11.04 | 13.55 | 12.76 | 9.73 | 8.86 |
| difference [%] | | −18.74 | | −0.35 | | −26.50 | | −5.83 | | −8.94 |
| Walking speed over 10 meters (as fast as he can) [seconds] | 9.25 | 7.63 | 10.16 | 9.36 | 13.22 | 9.19 | 11.57 | 9.90 | 7.96 | 7.55 |
| difference [%] | | −17.51 | | −7.87 | | −30.48 | | −14.43 | | −5.15 |
| TUG (Timed Up and Go) [seconds] | 12.15 | 10.79 | 10.83 | 10.46 | 19.29 | 15.13 | 11.81 | 11.65 | 9.30 | 7.47 |
| difference [%] | | −11.19 | | −3.42 | | −21.57 | | −1.35 | | −19.68 |
| TANDEM test [seconds] | >10 | >10 | >10 | >10 | >10 | >10 | 3 | >10 | >10 | >10 |
| difference [%] | | 0 | | 0 | | 0 | | >+233.33 | | 0 |
| SEMI TANDEM test [seconds] | 2.00 | >30 | 17.58 | 13.63 | 9.00 | >10 | 2.00 | 8.00 | <6 | >10 |
| difference [%] | | >+1400 | | −22.47 | | >+11.11 | | +300.00 | | >+66.66 |
| Backwards walking on 3 meters [seconds] | 6.16 | 6.09 | 8.55 | 3.84 | 17.36 | 13.91 | 10.00 | 6.50 | 4.35 | 4.02 |
| difference [%] | | −1.14 | | −55.09 | | −19.87 | | −35.00 | | −7.59 |
| Backwards walking on 3 meters (as fast as he can) [seconds] | 4.25 | 3.03 | 4.62 | 3.19 | 11.76 | 6.67 | 6.50 | 4.50 | 3.22 | 3.07 |
| difference [%] | | −28.71 | | −30.95 | | −43.28 | | −30.77 | | −4.66 |
| Chair Test (how many times he gets up and sits in 30 seconds) | 11.00 | 15.00 | 14.00 | 14.00 | 9.00 | 12.00 | 11.00 | 14.00 | 13.00 | 15.00 |
| difference [%] | | +36.36 | | 0.00 | | +33.33 | | +27.27 | | +15.38 |

The patients number 1 to 5 of the group treated with water according to invention had the following diseases and optionally additionally the following number of prescribed medicines/drugs:

Patient 1: Osteoporotic, multiple vertebral failures, arthritic-severe hypoacusia+4 medicines per day, hypertensive, anti-depressant drugs, sarcopenic;

Patient 2: rheumatoid arthritis, polyarthritis+4 medicines a day, walk with stick;

Patient 3: Padgett's disease-antidepressant drugs+4 medicines a day, arthritic, osteoporotic, previous cerebral ischemia;

Patient 4: Osteoporotic, multiple vertebral sagging, hypertensive+4 medicines per day, severe hypoacusia-arthritis, multi-natural encephalopathy; and Patient 5: Fibromyalgia, breast cancer, bladder tumor, hypovitaminosis D, osteoporosis, carotid sub-occlusion.

In particular, the above experimental results for the additional testing of walking parameters show that the water for use as a medicament according to the present invention provides for significant or even very significant increases of walking speed and almost all other above listed walking parameters, as can be gathered from the above tables. It is noted that for most of the tested walking parameters, e.g. walking speed in seconds, a percental decrease means an improvement. Because, e.g. for the walking speed in seconds, a decreased amount of seconds required for the distance of 10 meters means a higher walking speed.

By contrast, the placebo group treated with water being not according to the present invention shows no or at least no significant improvement of the walking parameters. Hence, it is additionally proven that surprising therapeutically effects are attained owing to the present medical use, whereby an alleged placebo effect can be ruled out also for the further tested walking parameters.

Push Tests

The following push tests were carried out before and after treatment of the patients with the water according to the present invention, wherein the patients were selected from the above groups described for the testing of the walking parameters. For the push tests, the CE certified dynamometer apparatus of THS-Therapeutics Solutions was adopted. The THS apparatus was used to put out of balance a patient. The patient was secured to a support sling or harness to avoid lateral falls. Using a dynamometer, the resistance/resilience at the lateral thrust of a patient was tested by determining as result of the effective lateral push, the load to the sling support, the displacement from the center of gravity and the displacement of the supporting foot for regaining the upright position (COP). For the testing, the test persons were positioned in orthostasis and secured in a sling, and received a defined lateral push placed on one of the two shoulders at the level of the deltoid region.

The dynamometer apparatus pushes at the height of the lateral deltoid, and various devices connected to the equipment and the test person detect the following:

the strength (in kg) has to be applied by the THS dynamometer apparatus in order to move the patient;

the load of the patient on the support sling or the leaning on the harness;

the displacement in mm of the center of gravity under the lateral thrust; and the path (in mm) of the supporting foot to resume the upright position, i.e. the pressure center.

Before/After results (for patient belonging to group 1)

| | Age [years]: | Sex: | Weight [kg]: | Height [cm]: |
|---|---|---|---|---|
| Patient's data: | 74 | F | 55 | 168 |

| Effective push [kg]: | | Load on the support sling [kg]: | | Center of gravity displacement [mm]: | | Pressure center [mm]: | |
|---|---|---|---|---|---|---|---|
| before: | after: | before: | after: | before: | after: | before: | after: |
| 2.80 | 4.09 | 4.20 | 2.70 | 1164 | 191 | 768 | 600 |
| 3.17 | 3.93 | 3.30 | 2.70 | 1201 | 334 | 862 | 730 |
| 3.93 | 4.19 | 4.50 | 2.70 | 992 | 207 | 714 | 766 |
| Ø *): | Ø: | Ø: | Ø: | Ø: | Ø: | Ø: | Ø: |
| 3.30 | 4.07 | 4.00 | 2.70 | 1119 | 244 | 781 | 698 |
| | +23% | | −32% | | −78% | | −11% **) |

*) Symbol "Ø" means average value of the three values listed above "Ø"
**) The percental values in last line indicate change between "before" and "after" values Before/after results (for patient belonging to group 4)

| | Age [years]: | Sex: | Weight [kg]: | Height [cm]: |
|---|---|---|---|---|
| Patient's data: | 79 | F | 45 | 153 |

| Effective push [kg]: | | Load on the support sling [kg]: | | Center of gravity displacement [mm]: | | Pressure center [mm]: | |
|---|---|---|---|---|---|---|---|
| before: | after: | before: | after: | before: | after: | before: | after: |
| 3.66 | 3.25 | 8.80 | 7.20 | 2287 | 1424 | 865 | 892 |
| 3.31 | 3.90 | 10.00 | 8.50 | 2145 | 765 | 1139 | 918 |
| 3.70 | 3.45 | 10.00 | 6.90 | 2145 | 693 | 817 | 795 |
| Ø *): | Ø: | Ø: | Ø: | Ø: | Ø: | Ø: | Ø: |
| 3.55 | 3.53 | 9.60 | 7.53 | 2192 | 960 | 940 | 868 |
| | +1% | | −21% | | −56% | | −8% |

*) Symbol "Ø" means average value of the two or three values listed above "Ø"
**) The percental values in last line indicate change between "before" and "after" values Before/after results (for patient belonging to group 2)

| | Age [years]: | Sex: | Weight [kg]: | Height [cm]: |
|---|---|---|---|---|
| Patient's data: | 67 | F | 56 | 166 |

| Effective push [kg]: | | Load on the support sling [kg]: | | Center of gravity displacement [mm]: | | Pressure center [mm]: | |
|---|---|---|---|---|---|---|---|
| before | after: | before: | after: | before: | after: | before: | after: |
| 3.27 | 4.54 | 2.90 | 2.60 | 441 | 248 | 1111 | 907 |
| 4.87 | 5.10 | 3.60 | 3.00 | 421 | 484 | 1012 | 1013 |
| 3.90 | 5.32 | 3.95 | 2.30 | 267 | 499 | 1007 | 1108 |
| Ø *): | Ø: | Ø: | Ø: | Ø: | Ø: | Ø: | Ø: |
| 4.01 | 4.48 | 3.48 | 2.63 | 376 | 410 | 1043 | 1009 |
| | +12% | | −24% | | +9% | | −3% |

*) Symbol "Ø" means average value of the three values listed above "Ø"
**) The percental values in last line indicate change between "before" and "after" values Before/after results (for patient belonging to group 3)

| | Age [years]: | Sex: | Weight [kg]: | Height [cm]: |
|---|---|---|---|---|
| Patient's data: | 77 | F | 62 | 160 |

| Effective push [kg]: | | Load on the support sling [kg]: | | Center of gravity displacement [mm]: | | Pressure center: | |
|---|---|---|---|---|---|---|---|
| before: | after: | before: | after: | before: | after: | before: | after: |
| 3.33 | 4.21 | 2.88 | 2.45 | 545 | 255 | 1227 | 988 |
| 3.77 | 4.33 | 3.79 | 2.98 | 601 | 345 | 1147 | 977 |
| 3.43 | 4.97 | 3.77 | 2.35 | 598 | 378 | 1159 | 956 |

-continued

| Effective push [kg]: | | Load on the support sling [kg]: | | Center of gravity displacement [mm]: | | Pressure center: | |
|---|---|---|---|---|---|---|---|
| before: | after: | before: | after: | before: | after: | before: | after: |
| Ø *): 3.51 | Ø: 4.50 +28% | Ø: 3.48 | Ø: 2.59 −25% | Ø: 581 | Ø: 326 −43% | Ø: 1177 | Ø: 973 −17% |

*) Symbol "Ø" means average value of the three values listed above "Ø"
**) The percental values in last line indicate change between "before" and "after" values Before/after results (patient belonging to group 5)

| Patient's data: | Age [years]; | Sex: | Weight [kg]: | Height [cm]: |
|---|---|---|---|---|
| | 88 | F | 75 | 163 |

| Effective push [kg]: | | Load on the support sling [kg]: | | Center of gravity displacement [mm]: | | Pressure center [mm]: | |
|---|---|---|---|---|---|---|---|
| before: | after: | before: | after: | before: | after: | before: | after: |
| 3.41 | 4.01 | 3.78 | 2.70 | 615 | 355 | 1131 | 929 |
| 3.77 | 4.18 | 3.60 | 2.67 | 631 | 376 | 1045 | 989 |
| 3.33 | 4.21 | 3.90 | 2.35 | 717 | 388 | 1133 | 877 |
| Ø *): 3.50 | Ø: 4.13 +18% | Ø: 3.76 | Ø: 2.57 −31% | Ø: 581 | Ø: 326 +43% | Ø: 1103 | Ø: 931 −15% **) |

*) Symbol "Ø" means average value of the three values listed above "Ø"
**) The percental values in last line indicate change between "before" and "after" values The above results of the push test show the following:
The effective push is improved for all test persons, wherein for three of the four persons, there is a very significant improvement of 12% or more;
the load on the supporting sling is improved for all test persons, wherein for all four test persons, the load on the supporting sling is very significantly reduced for 21% or more;
for the center of gravity displacement, it appears that this parameter strongly depends on the kind of the person (and his/her diseases) tested, because while there is a significant decrease of this parameter for two persons, there is a significant increase for the other two persons; and
for the pressure center, there is an improvement in terms of a decrease for all test persons, wherein for three test persons, there is a very significant decrease of 8% or more.

Pain Assessment

In addition to the above described testing of walking parameters and push test, a pain assessment by means of visual analogue scale (VAS) was done. The VAS pain assessment was carried out as follows: First, a defined pressure strength was applied to a test person by means of a digital algometer. Second, the test person classified his/her pain in a pain score being a numerical value range of 0 to 10, wherein 0 means no pain, and 10 means worst pain ever. By repeating the aforementioned steps of applying defined pressure strength, which is increased stepwise, and subsequent classification of the pain by VAS, the individual pain threshold of the test person before treatment with the water according to the present invention was determined.

Then, the test person was treated with the water according to the present invention. Thereafter, the pain assessment by means of VAS was carried out again, to find out whether or not there was a relief/decrease of pain.

It was surprisingly found that all test persons treated with the water according to the present invention had a decrease pain of about 40 to 60% compared to placebo group.

Annotations

In the following, questions regarding how electromagnetic energies like present energies (i), (ii) and (iii) can be stored in water, and how water applied with electromagnetic energies can be distinguished from normal water not applied with electromagnetic energies. Furthermore, it is shown how the (human) body is influenced by electromagnetic energies, and where in the body these energies are transmitted.

Premise

It is known that all humans and animals are potential subjects to attacks of an infectious type (bacterial, parasitic, viral) and even toxic (according to the research, we introduce at least 3000 toxins daily with diet and lung respiration). Furthermore, for humans, professional, family and modern life commitments lead to repeated fatigue, and therefore psycho-physical stress.

Bioelectrical medical devices that emit electromagnetic waves for therapeutic use do not exclude drug therapy, but favor a general improvement in health status.

Examples of biophysical medical therapies are: ultrasounds, radiotherapy, etc. [1]

In the university field, there are faculties dealing with bioelectromagnetism, such as that of professor Guglielmo D'Inzeo, who is professor in the field of bioelectromagnetic interaction at the La Sapienza University of Rome. Since 2016, he has been appointed a member of the International Commission on Non-Ionizing Radiation Protection (IC-NIRP) Commission.

Water is an abnormal substance. Its physical properties deviate considerably from homologous substances whose molecules are composed of 3 atoms.

A great deal of literature has been known since the 60s, a series of works show the presence of non-thermal effects of weak non-ionizing electromagnetic fields, on the living organism and on the biological system.

These effects have been observed for a wide range of frequencies, from visible light to microwaves, radio waves and quasi-static and static magnetic fields.

A considerable part of these works is connected to the role of cosmophysical and geophysical factors of life on earth, the other part of the work, is related to electromagnetic therapy in medicine.

There are several hypotheses that explain the effects of weak fields on the biological system, one based on the influence of electromagnetic fields on water properties.

The most convincing was shown in experiments with water previously exposed to electric, magnetic, electromagnetic, acoustic or vibrating fields, maintaining/storing the biological activity acquired for a sufficiently long time.

To date, a significant number of experimental works have appeared in which changes in the physicochemical properties of water and aqueous solutions are recorded under the action of weak fields of an electromagnetic nature and in addition to low and very low concentration of organic substances and inorganic with physical methods.

In view of reference [10], water, it becomes apparent that water is not just a pure substance consisting only of $H_2O$ molecules, but rather, water may maintain/store electromagnetic energies applied to the water.

Storing of Electromagnetic Energies in Water

An important characteristic of water is given by the polarity of its molecule. The shape of the water molecule, composed of three atoms, one of oxygen and two of hydrogen, is comparable to a tetrahedron with the oxygen atom in the center, two hydrogen atoms at two of the vertices, and two electrons not shared with the other two vertices. The electrons are more attracted towards the oxygen atom, being this more electronegative than hydrogen. Therefore, the bonds formed between the H atoms and the O atom are called "polar covalents", since they have a partial charge negative at the oxygen atom, and a partial positive charge at the hydrogen atoms.

A molecule that presents this imbalance of electric charges is called "electric dipole". Electric charges cause water molecules to be attracted to each other.

In nature, the water dipoles are randomly oriented following the laws of attraction that hold all the molecules together.

If water is subjected to electromagnetic fields, almost all of its dipoles (water molecules) tend to orient themselves according to the course (the direction of flow) of the electromagnetic field. [2]

That is, water has the ability to maintain the information received from the electromagnetic field or energies in the form of orientation of the dipoles that compose it. The electromagnetic field or energies by its definition is/are the set of waves that form the electric field or energies, with those of the magnetic field or energies that propagate on two perpendicular planes between them. The waves are the set of frequency and intensity of the electromagnetic field or energies and can have different shapes (sinusoidal, square, triangular, sawtooth etc.). Therefore, water subjected to an electromagnetic field or electromagnetic energies such as light or electrical energy maintain/store the direction impressed by the flow of the electromagnetic field, memorizes the frequency of the field or energy applied to it. The intensity and the time of application determine the duration of the storage of electromagnetic energy within the water [5].

How can Water Applied with Electromagnetic Energy/Energies be Distinguished from Normal Water not Applied with Electromagnetic Energy/Energies?

Water subjected to electromagnetic fields or energies changes its viscosity (and surface tension). Or rather, the viscosity of water, as the electromagnetic field or energy/energies increases, decreases the viscosity of the water applied with electromagnetic energy e.g. in the form of a magnetic field:

| Magnetic field: [Tesla] | Viscosity: mPas · s |
|---|---|
| 0 | 0.91 |
| 0.44 | 0.90 |
| 1.00 | 0.89 |
| 1.57 | 0.87 |
| 2.01 | 0.88 |
| 2.55 | 0.90 |
| 3.01 | 0.91 |

This increase in the viscosity of the water subjected to electromagnetic energy/energies such as electromagnetic fields increases the surface tension of the water or increases the cohesion between the water molecules, and consequently affects the meniscus of contact between water and the glass wall. The meniscus is the radius of curvature, which assumes the superficial water veil in contact with the glass, in the case of water the meniscus is concave (curvature facing upwards). [20]

The smaller the diameter of a water container, the more pronounced is the meniscus. Therefore, using a container with a small graduated diameter (burette), one can measure the differences between the two radii of curvature (meniscus), of the two burettes containing the water not subjected to a magnetic field and the one subjected to a magnetic field. [20]

Water is the best universal solvent. It stores information (received from the solutes with which it comes into contact) aggregating in particular forms groups of molecules called "clusters" (which have their own EMF—Electro Magnetic Field), and releases it (exchanges). Only when water comes into physical contact with other liquids, a compensation for "difference in IT potential" takes place. Thereby, the medium, or the interface to obtain this exchange is the CEM of the two liquids (water and informed clusters), come to "to meet" by contact:

http://www.medicinaecologica.it/
medicina%20ecologica%20-
%20Memoria%20dell'Acqua.html Does Water Applied with Electromagnetic Energy/Energies Undergo Chemical and Physical Changes?

Water exposed to the influence of electromagnetic energy in the form of e.g. a weak magnetic field is magnetized for a very short time. Some publications have described the effects of the electromagnetic field (EMF) on water molecules. These effects include: Changes in viscosity, surface tension, light refraction index, electrical conductivity and light absorption. [6]

The physical properties of water change, while the chemical composition remains unchanged.

The phenomenon of magnetization is explained by the fact that the magnetic field deforms the structure of water. It is known that water is a set of molecules arranged in a certain sense. If we let water pass through a series of alternating and powerful magnetic fields, electric charges are added that change both the sense and the displacement of the ions, so that the water becomes magnetized acquiring the ability to prevent the formation of microcrystals:

https://arteruffini.wordpress.com/medicina-alternativa/
acqua-magnetizzata/

It has been shown that magnetized and non-magnetized water have different rates of UV absorption:

https://www.biomag.it/magnetizzazione-dell-acqua

In the human body, about 60 trillion cells immersed in a liquid called water are born, reproduce, function, transmit, receive information and die obeying the laws of electromagnetism, behave in practice as electromagnetic oscillators and this applies to all living tissues:

https://arteruffini.wordpress.com/medicina-alternativa/
acqua-magnetizzata/

The aforementioned professor Piccardi managed to distinguish three states of "activation" (magnetization) of water, which he called type "C" (not activated water), "T" and "R". He also noted that the activated water could transmit the activation status (magnetization) also to other water through the walls of a container, but modifying the effect according to whether the walls of the container were insulating or conductive.

Piccardi, in a conference at the Italian Chemical Society held at the Institute of General Chemistry of the University of Genoa on Saturday 29 Apr. 1939, summed up the main features of the activation status, specifically referring to the water:
1) Water activation is not instantaneous, but requires a certain duration of the activating action;
2) Water retains its new properties for a very long time, at least for about four days (in fact, there was a much longer time, from twenty days to many months, depending on the chemical species present in the water and the type of energy transmitted;
3) Water does not lose its new properties due to freezing or distillation;
4) The activated water "T" or "R" acts on the common water ("C") through electrically insulating walls, transforming it into water also "T" or "R";
5) The activated water "T" or "R", acts on the common water ("C") through metal walls, but transforming it into water "R" or "T". It is an inverse action that constitutes a singular effect due to metals; and
6) Other liquids may be able to behave like water.
[22]

With What Types of Energy can Water be Magnetized? What Magnitudes of Magnetism are Known in Literature?
Water can be magnetized by means of:
permanent magnets, 3000 Gauss (300 µt); and/or by low intensity low frequency electromagnetic fields.

much weaker alternate field, $B_{ac}$, $[B_{ac} \sim 10\text{-}3\ B_0]$ whose frequency coincides with the frequency of the cyclotron $v=qB_0/2\Pi m$ of the selected ion. Consequently, there are ionic phenomena that last up to 20 s and with amplitudes up to 10 nÅ. Energy exchanges induced by thermal agitation (the "KT problem") seem to have no role. We analyzed this problem in the framework of coherent quantum electrodynamics, reaching the following conclusions:
(a) As has been shown in previous articles, water molecules in liquid and solute ions are involved in their ground state in ordered coherent configurations;
(b) the ions are able to move without collisions between them in the interstices between the water coherence domains; and
(c) due to consistency, ions can follow classical orbits in magnetic fields. [28]

It has been shown that it is possible to foresee the possibility that the coherent interaction between the water's electric dipoles and the field/energies that radiates it, carries out the very important task of generating ordered structures in macroscopic domains (i.e., within a few hundred micron), which could therefore play a fundamental role in the organization of the animate as well as the living matter in the wonderful ways in which physical analysis is incessantly revealing. Obviously, further research is needed in this direction. [29]

| The sources of bio-information frequencies: | How to print a frequency in the water memory: | How to erase the frequencies stored in the water: | How to measure the frequency stored in water: |
| --- | --- | --- | --- |
| body magnetic field | by proximity | closed steel box | pair of electrodes connected to a differential amplifier |
| acupuncture meridians | percussion (agitation) | dilution (using prime numbers) | single electrode (reveals only field A) |
| Chakra points | for impulses (agitation) | | response of a dowser (from µHz to THz) |
| chemical marking | permanent magnets | | modulated light diffusion and its images |
| diffuse light and images | ferrite toroids | | |

Water subjected to constant magnetic fields (permanent magnets) of varying intensity produced physical changes in the properties of water.
Change in Specific Heat (i.e. Change in Boiling Point):

| Boiling temperature: [° C.] | Tap water with magnetic field: [mT] |
| --- | --- |
| 99.29 | 0 |
| 98.17 | 100 |
| 97.61 | 200 |
| 97.23 | 300 |
| 98.02 | 400 |

Other studies talk about the behavior of water, when subjected to high frequency electromagnetic fields, of the order of the Giga Hertz, but they are not treated here, as they are harmful to living matter. [8]

A recent experiment on a physical, non-biological system of room-temperature ions has shown that microscopic ion currents can be induced by simultaneously applying two parallel magnetic fields, a rather weak static field, $B_0$ and a Why is a Human being or Animal Influenced by Electromagnetic Fields?

The water present in living organisms is different from the water that flows in rivers or fills the oceans, since it has additional properties, namely properties of quantum physics, in particular coherence. Namely, the water molecules that make up our body form a "coherent system", which means that the individual water molecules are related to each other. In other words, all the water molecules of an organ are in "phase", they share the same content of information, or the electrons of the atoms that make up the water, oscillate in sync at the same frequency. The human body is a complex of biological organs, one different from the other. The human body then develops specific electromagnetic signals, which can be measured today. [11]

When a child is conceived, the heart starts beating before the brain is formed. This led doctors to wonder where the intelligence needed to start and regulate the heartbeat comes from. To the surprise of the medical world, scientists at the Heart Math Institute in California have discovered that the heart has its own brain composed of around forty thousand cells. Furthermore, they showed that the human heart generates the largest and most powerful energy field among all those generated by the other organs of the body, including the brain inside the skull. They discovered that this electromagnetic field has a diameter that extends from two and a half meters to three meters, with the axis centered in the heart. The electromagnetic field generated by the heart permeates every cell and, similarly to information carried by radio waves, can act as a synchronizing signal for the whole body. The evidence experimental shows that this energy, not only is transmitted internally to the brain, but is also transposable by other subjects who are within its range of action. The electric field that is measured by the electrocardiogram (ECG) is approximately 60 times larger in magnitude than that generated by brain waves recorded by an electroencephalogram (EEG). The magnetic component of the heart field, which is approximately 5000 times more powerful than that produced by the brain, is not hindered by tissues and can be measured up to a few meters away with a Superconducting Quantum Interference Instrument (SQUID) based on magnetometers. [25]

The magnetic fields generated by the brain and other organs of the human body are very weak, of the femtoTesla order (10-15 T), to perform these measurements on the human body, it is necessary to work inside a shielded chamber with a magnetic field terrestrial which varies from 68 µT (10-6 T) at the equator to 20 µT at the poles.

The magnetic fields generated by the brain have specific, measurable frequencies divided into the following ranges:

| Wave: | from: | to: |
| --- | --- | --- |
| Delta | 0 Hz | 4 Hz |
| Theta | 4 Hz | 8 Hz |
| Alpha | 8 Hz | 13 Hz |
| Beta | 13 Hz | 25 Hz |
| Gamma | 26 Hz | 50 Hz |

Static magnetic fields can have significant clinical utility while pulsed magnetic fields (PEMF) show more powerful effects on the biological system. [19]

Ex vivo studies have shown that electromagnetic fields pulsed at 75 Hz (1.5 mT of magnetic induction) increase the synthesis of the proteins that make up the extracellular matrix of cartilages (proteoglycans), thus decreasing the catabolic effect of inflammatory cytokines. Investigations carried out in vitro have shown that a 30-minute exposure to the pulsed fields described above causes an increase in the adenosine-A2A receptor bond which results in an increase in the production of nitrogen oxide with a consequent decrease in the efficacy of pro-inflammatory cytokines, responsible for in turn of the degradation of the cartilaginous matrix. Furthermore, for exposures longer than 6 hours there is also an increase in the production of chondrocytes. [26]

Recent evidence shows that MSM (Mesenchymal Stromal Cells) found in joint tissues can differentiate to repair damaged tissue, this repair function can be suppressed by the inflammatory environment. The extremely low pulsed low frequency electromagnetic field (PEMF), a form of biophysical stimulation, has an anti-inflammatory effect causing CSM differentiation. PEMFs increase the functional activity of CSMs and improve the differentiation of chondrocytes and osteocytes, accelerate cell differentiation, increase collagen deposition. [21]

Excerpt from an Interview with Prof. Guglielmo D'Inzeo—Full Professor of Bioelectromagnetic Interaction at the La Sapienza University of Rome How have the investigative techniques and methodologies evolved in molecular interaction studies aimed at investigating non-thermal effects? The techniques and methods of investigation at the molecular level have been adopted in the field of bioelectromagnetism for over twenty years. Only recently has the technological evolution and the consequent increase in computing capacity made available the necessary tools to be able to apply these numerical models in practice and fully exploit the theoretical knowledge already developed.

Similarly, computational molecular dynamics techniques have evolved, which are more typical of chemistry and are applied to bioelectromagnetism by adding the presence of the electromagnetic field to the simulation control variables. In reality, the application of these techniques to chemistry has also shown that the molecules communicate in "electromagnetic mode", since the molecular reactions are controlled by the interaction between electrons and the relative fields generated. Electromagnetic fields are therefore the basis of the functioning of biological systems, even in the absence of an external field. [27]

Towards which applications do research on interaction with EMFs at the cellular level address today?

. . . Molecular simulations allow us to study which type of electric field is most effective in different therapeutic applications . . . . Considering that the basic mechanisms are not yet fully known, it can be said that this type of technique applied at the clinical level has great potential. [27]

Where is the Electromagnetic Signal Transmitted?

We have seen how the propagation of the electromagnetic field through connective tissues takes place but with a loss of signal strength, so it is necessary to give the field such power as to overcome the layers of connective tissue to reach the organ to be treated. It is possible to overcome this problem by associating the PEMF technique with the knowledge of the stimulation points of the acupuncture energy channels. The classical Chinese theory of acupuncture states that there are 12 main meridians that are used as a link between the body and the head (brain that governs all the organs), other accessory meridians extend internally to the body and reach all internal organs. In classical acupuncture are needles that stimulate the various end points under the skin that connect the internal organs to be treated. [14]

Study on the emission of photons from the hands in the short term. The human eye is not the sensitivity so strong as to perceive the emission of photons, therefore we use equipment suitable for the purpose, the so-called photomultiplier tubes. Experimental work has been done with the aim of gathering more information on the dynamics of the fluctuation of the emissions of human photons in the 24-hour interval, since the data concerning the dynamics of the emission of human photons found in the literature are rather scarce and oriented more on long-term observation, weeks and months time intervals. From this research it was found that diurnal fluctuations in the intensity of photonic emissions and the asymmetry of left-right hands are not negligible. The knowledge of the diurnal rhythms of the emission of intensity and symmetry of photons is crucial for the evaluation of any further experiments based on the comparison between left/right anatomical positions, to avoid false conclusions. However, the trend of these emissions must be deepened through further research, this new set of data can serve as a perspective for a non-invasive diagnostic tool. [16]

The emission of photons from the palm and back of the hands can be one of the ways to verify the change in the biological state of the human body when subjected to constant magnetic fields.

The system provides for the measurement of the emission of photons from the hands using a darkroom within which there are photon counters, data is recorded for 3 minutes and stored.

Subsequently, small magnets are placed in 17 points of stimulation of the acupuncture of the hand and right foot, for 1 hour; after which the new measurement of the emission of the photons and their storage is performed.

Analyses of the data of the two measurements on a sample of 37 people showed that the emission of photons is different in relation to the measurements taken before and after stimulation with permanent magnets. [19]

A study based on the research on the correlation age and emission power of photons from hands, has shown the existence of a significant relationship between the chronological age and the emission of ultra-weak photons from the hands; or a positive correlation between the emission force of photons with chronological age. [15]

LIST OF REFERENCES CITED IN THE ANNOTATIONS

List of references cited in the Annotations

| Reference No. | Title: | Author and/or publication date: |
|---|---|---|
| [1] | Le meraviglie dell'acqua. Il mistero biofisico che ci dona la vita. | P. Spaggiari, C. Tribbia (May 2007) |
| [2] | Medicina biofisica con acqua informata: www.lionspratocastello.it/pdf/sermoneta acqua.pdf | E. Sermoneta |
| [3] | Water system Aqua technology For the 21st Century | May 2018 |
| [4] | Electromagnetic and magnetic vector potential bio-information and water | C. W. Smith (August 2015) |
| [5] | Magnetic and Electric Effects on Water | April 2018 |
| [6] | Diverse biological effects of electromagnetic-treated water | M. Yamabhai et al. (November 2013) |
| [7] | Effect of magnetic field on the physical properties of water | Y. Wang et al. (December 2017) |
| [8] | Changes in the state of water, induced by radiofrequency electromagnetic fields | Evgenii E. Fasenko et al. (April 1995) |
| [9] | Illuminating water and life: Emilio Del Giudice | Mae-Wan Ho (June 2015) |
| [10] | Water is a Sensor to Weak Forces Including Electromagnetic Fields of Low Intensity | V. I. Lobyshev (2005) |
| [11] | Il ritorno della memoria dell'acqua | Indigo Stargate (March 2019) |
| [12] | The structural memory of water persists on a picosecond timescale | J. Hunger (September 2015) |
| [13] | Mechanism of low level microwave radiation effect on nervous system | H. Hinrikus et al. (August 2016) |
| [14] | Human ultraweak photon emission and the Yin Yang Concept of Chinese Medicine (fondamentale) | Roeland van Wijk et al. (July 2010) |
| [15] | Ultra-weak photon emission of hands in aging prediction | Xin Zhao, Roeland van Wijik et al. (July 2016) |
| [16] | Spontaneous Ultra-Weak Photon Emission from Human Hands Is Time Dependent | M. Cifra, Roeland van Wijik et al. (June 2007) |
| [17] | Measuring resistance in the body | 2007 |

-continued

List of references cited in the Annotations

| Reference No. | Title: | Author and/or publication date: |
|---|---|---|
| [18] | Far infrared radiation (FIR): its biological effects and medical applications | F. Vatansever et al. (November 2012) |
| [19] | Magneto-Acupuncture Stimuli Effects on Ultraweak Photon Emission from hands of Healthy persons | Sang-Hyun Park et al. (January 2009) |
| [20] | Menisco di una sostanza liquida.pdf http://www.itisforli.it/materiale/chimical/ menisco.pdf | F. Carroli (20 Sep. 2006) |
| [21] | Targeting Mesenchymal Stromal Cells/Pericytes (MSCs) With Pulsed Electromagnetic Field (PEMF) Has the Potential to Treat Rheumatoid Arthritis https://www.ncbi.nlm.nih.gov/pmc/articles/ PMC6409305/ | Christina L. Ross et al. (4 Mar. 2019) |
| [22] | Considerazioni chimico-fisiche intorno al funzionamento del dispositivo Toem ed all'effetto Scali http://www.scienzemedicolegali.it/ documenti/archivio/brevetto-toem.pdf | |
| [23] | ICNIRP Guidelines-On limits of exposure to static magnetic fields | International Commission on Non-Ionizing Radiation Protection |
| [24] | ICNIRP Guidelines-For limiting exposure to time-varying electric and magnetic fields (1 Hz-100 kHz) | International Commission on Non-Ionizing Radiation Protection |
| [25] | L'Uomo è un'antenna Bibliografia\Bibliografia R\25 2013 07 23 L'uomo è una antenna.pdf | (23 Jul. 2013) |
| [26] | Elettra 2000 Informa Bibliografia\Bibliografia R\26 2013 03 02 Elettra 2000 informa.pdf | (2 Mar. 2013) |
| [27] | Elettra 2000 Informa Bibliografia\Bibliografia R\27 xxxx xx xx Intervista D'Inzeo.pdf | |
| [28] | On the "Unreasonable" Effects of ELF Magnetic Fields Upon a System of Ions | E. Del Giudice et al. (25 Feb. 2002) |
| [29] | Water as a Free Dipole Laser Physical Review Letters | E. Del Giudice et al. (29 Aug. 1988) |

What is claimed is:

1. A method for providing water irradiated with electromagnetic energies, wherein the method comprises:
   (A) a step of providing water;
   (B) a step of applying electromagnetic energies to the water of step (A), wherein the electromagnetic energies are in the form of:
   (i) light energy with a wavelength of between 500 and 700 nm,
   (ii) light energy with a wavelength of between 701 and 1050 nm, and
   (iii) an electrical energy with a maximum voltage of 240 V,
   and the electromagnetic energies are simultaneously applied to the water,
   wherein at least one of the electromagnetic energies (i), (ii) and (iii) is applied to the water in the form of trains of pulses having at least two discrete frequencies, wherein a first frequency is between 0.1 to 10 Hz and a second frequency is between 40 and 1500 Hz,
   wherein for each of light energies (i) and (ii), the amount of energy is between 1.5 to 2 J, and for the electrical energy (iii), the amount of electrical energy is up to 0.4 J.

2. The method according to claim 1, wherein the water has at least one of the following features a), b) and c):
   a) the water is tap water, distilled water, osmosis water, reverse osmosis water or a mixture thereof;
   b) the water contains sodium chloride;
   c) the water contains sodium chloride in an amount of at most 330 g/l, or 1 to 35 g/l, or 4 to 30 g/l, or 8 to 10 g/l.

3. The method according to claim 1, wherein the water is in the form of water alone or the water is comprised in a material selected from a fabric, a non-woven, medical patches, a cream formulation, a gel formulation, an ointment formulation, an aqueous solution, a product for dental hygiene, a food and a drink; or water is used alone or comprised in a material selected from a fabric, a cream formulation, a gel formulation, an ointment formulation, an aqueous solution; or water is used alone or comprised in gauze fabric or terry fabric; or water is used alone or comprised in gauze fabric.

4. The method according to claim 1, wherein the electromagnetic energies (i), (ii) and (iii) are simultaneously applied to the water for at least 5 min, or 7 min to 2 h, or 8 min to 1 h, or 9 min to 35 min, or 9 min to 30 min, or 10 to 20 min.

5. The method according claim 1, wherein in the pulses having at least two discrete frequencies, the first frequency is between 0.5 to 7.5 Hz and the second frequency is between 60 and 220 Hz; or the first frequency is between 0.5 to 5 Hz and the second frequency is between 70 and 200 Hz; or the first frequency is between 0.8 to 3.2 Hz and the second frequency is between 80 and 190 Hz; or the first frequency is 1 Hz, 2 Hz or 3 Hz, and the second frequency is 85 Hz, 100 Hz or 180 Hz; or the first frequency is 1 Hz and the second frequency is 180 Hz, the first frequency is 2 Hz and the second frequency is 100 Hz, or the first frequency is 3 Hz and the second frequency is 85 Hz.

6. The method according claim 1, wherein (iii) the electrical energy has a maximum voltage of 200 V, or a maximum voltage of 150 V, or a maximum voltage of 110 V, or a maximum voltage of 90 V, or a maximum voltage of between 50 and 85 V.

7. The method according claim 1, wherein each pulse has a duration of between 50 and 1000 µs, or of between 80 and 500 µs, or of between 90 and 350 µs; and/or
   between the pulses, there is a pause time of between 0.5 and 20 s in which there is no pulsed electromagnetic energy.

8. The method according claim 1, wherein for each of light energies (i) and (ii), the amount of energy is between 1.7 to 1.9 J; and/or for electrical energy (iii), the amount of energy is between 0.05 to 0.3 J, or between 0.1 to 0.25 J.

9. The method according to claim 1, wherein the water applied with electromagnetic energies (i), (ii) and (iii) has a boiling point below 99.29° C., or below 99.10° C., or below 98.90° C., or below 98.70° C., or below 98.50° C., or below 98.30° C.; and/or
   the water applied with electromagnetic energies (i), (ii) and (iii) has a viscosity below 0.91 mPa·s, or below 0.90 mPa·s, or between 0.87 to 0.90 mPa·s.

\* \* \* \* \*